United States Patent [19]

Breese

[11] 4,432,833

[45] Feb. 21, 1984

[54] PULP CONTAINING HYDROPHILIC DEBONDER AND PROCESS FOR ITS APPLICATION

[75] Inventor: John A. Breese, Appleton, Wis.

[73] Assignee: Kimberly-Clark Corporation, Neenah, Wis.

[21] Appl. No.: 352,399

[22] Filed: Feb. 25, 1982

Related U.S. Application Data

[63] Continuation-in-part of Ser. No. 150,885, May 19, 1980, abandoned.

[51] Int. Cl.³ .............................................. D21H 3/12
[52] U.S. Cl. .................... 162/158; 162/100; 162/201; 604/374; 604/375
[58] Field of Search ............... 162/158, 100, 184, 185, 162/182, 135, 201; 128/284; 604/374, 375

[56] References Cited

U.S. PATENT DOCUMENTS

| | | | |
|---|---|---|---|
| 3,554,863 | 1/1971 | Hervey et al. | 162/158 |
| 4,144,122 | 3/1979 | Emanuelsson | 162/158 |
| 4,303,471 | 12/1981 | Laursen | 162/158 |
| 4,351,699 | 9/1982 | Osborn | 162/158 |

*Primary Examiner*—Peter Chin
*Attorney, Agent, or Firm*—Howard Olevsky; R. Jonathan Peters; Gregory E. Croft

[57] ABSTRACT

The invention provides a cellulosic pulp having reduced interfiber bonding and therefore reduced physical strength while maintaining excellent hydrophilic properties. The pulp is produced by treating the cellulosic fibers with a hydrophilic debonder having the general formula:

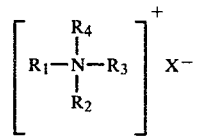

wherein:
R$_1$=methyl, ethyl, propyl, hydrogen or hydroxyethyl,
R$_2$=methyl, ethyl, propyl or [ethylene oxide]$_n$ where N=1 to 50,
R$_3$=aliphatic chain of at least 4 carbon atoms,
R$_4$=[ethylene oxide]$_n$ or [propylene oxide]$_n$ with N=1 to 50,
X—Cl, I, Br, SO$_4^-$, PO$_4^{--}$, CH$_3$CO$_2$.

10 Claims, No Drawings

PULP CONTAINING HYDROPHILIC DEBONDER AND PROCESS FOR ITS APPLICATION

CROSS REFERENCE TO RELATED APPLICATION

This application is a Continuation-in-Part application of U.S. Ser. No. 150,885, filed May 19, 1980 by the same inventor, now abandoned.

FIELD OF THE INVENTION

This invention relates to a pulp having low physical strength and excellent hydrophilic properties produced by the incorporation of a hydrophilic debonder of the quaternary amine type.

BACKGROUND OF THE INVENTION

Over the past several years there have been continuing attempts to improved specific properties of cellulosic pulp-derived products by utilization of a variety of debonding agents. These debonding agents quite frequently include a quaternary amine component because of the high degree of substantiveness of this moiety for cellulose. Examples of quaternary amine debonders can be found in U.S. Pat. Nos. 3,554,863; 3,554,862; 3,395,708; and No. Re. 26,939 issued to Laurence R. B. Hervey, et al. Additional examples of such debonders can be found in U.S. Pat. No. 3,617,439 issued to Benjamin E. Chapman, Jr., Canadian Pat. No. 1,020,935 issued to Louis S. Hurst, et al, British Pat. Nos. 1,282,593 and 1,180,801 also issued to Hervey, and U.S. Pat. Nos. 3,556,931; 4,510,246 and 3,356,526.

Until fairly recently it has been axiomatic in the pulp and paper industry that the debonding function was inversely related to hydrophilicity, i.e. the increase in efficiency of debonding as represented by reduced physical strength would result in reduced absorbent rate and total absorbent capacity in subsequent product applications of the pulp.

Typical debonders are long chain cationic surfactants, preferably with at least 12 carbon atoms in at least one carbon chain. Specific non-limiting examples of these would be fatty dialkyl quaternary amine salts.

The mechanism for debonding with these materials occurs as follows. The polar quaternary portion of the surfactant is strongly attracted to the negatively-charged cellulose fibers. It is this strong electrostatic interaction which leads to the excellent substantivity of the quaternary amine molecule for the cellulose fibers. This interaction leaves the hydrophobic portion of the surfactant molecule exposed thus giving the fiber surface hydrophobic properties, which interferes with the ability of inter-fiber bonds to form resulting in decreased physical strength of the pulp. This hydrophobic surface on the cellulose fibers also results in a pulp which exhibits increased hydrophobic behavior relative to the same pulp without the surfactant. In applications for highly absorbent products the increased hydrophobicity of the treated pulp is unsatisfactory.

U.S. Pat. No. 4,144,122 issued to Jan G. Emanuelsson, et al discloses a class of quaternary amine compounds containing repeating hydrophilic ethylene oxide units at two of the quaternary positions. These ethylene oxide units are attached to the quaternary nitrogen by propylene linkages in each case. They are also characterized by an ether linkage to an aliphatic chain at both positions. According to U.S. Pat. No. 4,144,122, debonding is accomplished while the hydrophilic character of the debonded pulp is improved when compared with conventionally debonded pulps. This relatively improved hydrophilicity is due to the reduction of the hydrophobicity of the alkyl chains due to the presence of the ethylene oxide units. Now, when the interaction of the cationic quaternary amine and the anionic cellulose fibers occurs, the portion of the molecule exposed is of decreased hydrophobicity, and the cellulose fiber surface of improved hydrophilicity, relative to that found for conventional debonders.

According to this invention, another class of debonding compounds has been identified which produces pulp which is more hydrophilic than the pulp produced according to U.S. Pat. No. 4,144,122. The compounds used in this invention use hydrophobic components of the quaternary amine as separate moieties from the hydrophilic components.

When the quaternary amine used in this invention interacts with cellulose fiber, reduced inter-fiber bonding again occurs. However, with the compounds utilized herein, both hydrophobic and hydrophilic portions of the molecules are exposed resulting in a cellulose fiber surface of hydrophobic and hydrophilic regions. Unexpectedly, this results in a pulp of greatly improved absorbent properties. While the applicant can not completely explain the mechanism by which the presently disclosed compounds accomplish their beneficial action, and further does not wish to be bound by theory, it is likely that as the cellulose fibers come into contact with the liquid to be absorbed, a hydrophilic pathway is always presented by which formation of the absorbing liquid-cellulose fiber interface can be accomplished more easily than if only a hydrophobic cellulose surface was presented. That the class of molecules described by this invention achieve hydrophilic debonding by a more efficient mechanism than occurs for the class of molecules described by Emanuelsson is clear when a compound used in this invention is directly compared with a compound which is structurally similar but covered by the Emanuelsson patent as shown in Example 4. In each case the molecules described by this invention are superior.

SUMMARY OF THE INVENTION

According to this invention, a hydrophilic debonder having the general formula:

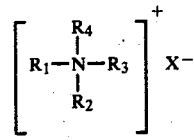

wherein:
$R_1$=methyl, ethyl, propyl, hydrogen or hydroxyethyl,
$R_2$=methyl, ethyl, propyl or [ethylene oxide]$_n$ where N=1 to 50,
$R_3$=aliphatic chain of at least 4 carbon atoms,
$R_4$=[ethylene oxide]$_n$ or [propylene oxide]$_n$ with N=1 to 50,
X=Cl, I, Br, $SO_4^-$, $PO_4^{--}$, $CH_3CO_2$.

Compounds of this general formula actually show increased capacity for producing hydrophilic pulp when compared to similar compounds with the structure described in U.S. Pat. No. 4,144,122. Any one or more of the selected chemicals which are defined by the general formula set forth above may be introduced into the pulp or pulp sheet at a number of different places during the commercial pulp sheet forming operations. Due to the hydrophilic properties of the pulp after treatment with the debonder, the utility for products produced from this pulp varies from fluff used in conventional absorbent materials such as sanitary napkins and diapers to absorbent sheet stock such as paper towels. It should be noted with regard to diapers that a series of absorbent tests indicates a substantial increase in the absorption of urine when compared to the more conventional debonding agents and therefore, the products of this invention have particular utility in diaper products. (Diapers and diaper products as used herein are designated specifically to include all incontinence pads and products whether they are designed specifically to be worn by an infant or adult or whether they are in sheet form such as for use with incontinent children or adults in a hospital or nursing home environment). These properties are further delineated in the examples presented.

Quaternary ammonium compounds according to this invention should be added to the web cellulose pulp after delignification or bleaching, either before or during the formation into sheets or continuous webs on the cellulose pulp machine or a paper machine. The compounds are preferably in an aqueous carrier in a concentration within the range of from about 1% to about 15% by weight of the debonder. These treating solutions may also contain conventional viscosity reducing additives such as ethanol, propanol, monoethyl ether or diethylene glycol and other additives traditionally associated with the debonder addition process. The weight amount of the "active" novel debonder based upon the bone dry weight of the cellulose ranges from about 0.05% to about 5.0% and preferably between about 0.2% to about 2.5%.

The treating solution can be applied by mixing with a pulp slurry. It can also be applied by spraying or dipping, by kissing rolls or any other suitable technique. Following application, the treated cellulose pulp or paper can be dried in the usual manner. The treated cellulose may be fiberized into cellulose fluff as mentioned above for utilization in various hygienic products. In all other ways, paper and pulp processing related to the handling of pulp containing these compounds is essentially conventional.

A non-exclusive listing of products which fall within the definitional category of this invention and are currently commercially available would include those sold under the trademark ETHOQUAD by Armak Industrial Chemical Division of Akzona, Inc. of Asheville, N.C. These compounds are generally used for antistatic agents, electroplating bath additives and dye-leveling agents. Also useful are the class of compounds sold under the EMCOL trademark by Witco Chemical Company, Inc., New York, N.Y. used for similar purposes.

EXAMPLE 1

This example compares the hydrophilic debonding capabilities of molecules made in accordance with this patent with that of debonders currently in wide use in the pulp and paper industry. In this example the debonding ability of the additives is measured by burst strength according to TAPPI Standard Method T403 OS-76 and tensile strength, TAPPI Standard Method T494 OS-70. Water absorbency rate is determined by the strip test. In this method, test specimens are obtained from debonder treated handsheets by cutting three $1'' \times 3''$ randomized strips from each sheet. It is found that 5 sheets are appropriate for each test condition. Each strip is marked at 0.5 cm intervals for 3.5 cm starting from the edge of the 1" end.

Deionized water (surface tension = 72 dyne/cm) is placed in a two-liter glass bottle. The test strip is affixed in the bottle just above and perpendicular to the liquid surface. The level of the liquid is then adjusted until the liquid surface is just in contact with the strip. The sheet then absorbs the liquid and it rises up the strip. A light source behind the bottle aids in observing the liquid rise. When the liquid contacts the first 0.5 cm line, a timer is started. Then each time the liquid touches the next higher 0.5 cm line, the time is recorded. This results in 90 measurements for each condition (3 strips/sheet × 6 measurements/strip × 5 sheets/test condition).

The rate of fluid migration up the strip is determined by fitting the data to a regression of this migration up the strip vs. the square root of time required. The square root arises out of consideration of the Lucas-Washburn equation. The fits are excellent with $r \geq 0.98$ in all cases considered. This results in rates calculated to better than ±4%. All data contained are corrected for density. The data can be used to determine the rare (volume) water absorbency from consideration of the dimensions and density of the strips. The rate (volume) water absorbency for a strip can be converted to the rate (volume) water absorbency for diaper fluff by multiplying by a mathematical factor related to the dimensions of cellulose fluff in a diaper. The relationship between the calculated values for diaper fluff absorbency and those measured are better than +5%.

For all tests described, hand sheets having 60 lb/3000 ft² basis weight were produced. Three compounds made according to the general formula of this invention were tested as debonding agents and they were as follows:

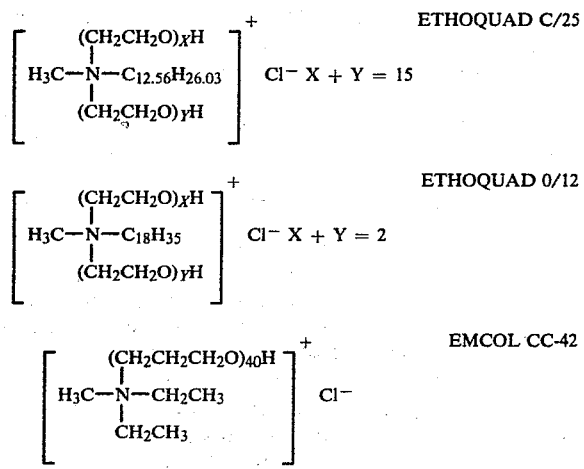

These compounds were tested against a group of conventional debonders composed of: QUAKER 2006, a debonder now being sold by Quaker Chemicals of Barrington, Ill.; ARQUAD 2HT-75, a commercially available debonder sold by Armak Chemical, Inc., Chicago, Ill.; and BEROCELL 579, 582 and 584 made in accordance with U.S. Pat. Nos. 3,972,855 and 4,144,122. The structure of the individual BEROCELL compounds are not specifically indentified other than by patent number; the ARQUAD compound is a quaternary amine with a methyl group at $R_1$ and $R_2$ and saturated $C_{18}$ groups at $R_3$ and $R_4$. The QUAKER 2006 compound is not specifically identified by the Quaker Company but it is believed to have a five member ring structure containing two nitrogen atoms with one nitrogen double bonded to one of the carbons in the ring structure and the other nitrogen having two substituent groups bound thereto in addition to the bonding associated with the ring structure.

When compared according to the tests described above, the following table represents the values so determined:

TABLE I

| Additive | Pulp | Burst (P.S.I.) | Tensile (lbs/in) | Water Absorbency (cm/sec ½) | Water Absorbency (ml/sec ½) | Diaper Fluff Absorbency (ml/sec ½) |
|---|---|---|---|---|---|---|
| NONE | SSK | 9.02 | 5.47 | .63 | .336 | 44.1 |
| EMCOL CC-42 | SSK | 4.19 | 3.90 | .68 | .363 | 47.6 |
| EMCOL CC-42 | SSK | 4.00 | 3.44 | .64 | .341 | 44.8 |
| EMCOL CC-42 | SSK | 3.33 | 3.10 | .63 | .336 | 44.1 |
| ETHOQUAD C/25 | SSK | 6.31 | 4.57 | .57 | .304 | 39.9 |
| ETHOQUAD C/25 | SSK | 6.23 | 4.65 | .55 | .293 | 38.5 |
| ETHOQUAD C/25 | SSK | 5.37 | 4.52 | .55 | .293 | 38.5 |
| ETHOQUAD C/25 | SSK | 5.32 | 4.49 | .54 | .288 | 37.8 |
| ETHOQUAD 0/12 | SSK | 5.44 | 4.60 | .64 | .341 | 44.8 |
| ETHOQUAD 0/12 | SSK | 4.85 | 3.83 | .60 | .320 | 42.0 |
| ETHOQUAD 0/12 | SSK | 4.74 | 3.03 | .57 | .304 | 39.9 |
| QUAKER 2006 | SSK | 6.38 | 3.85 | .31 | .165 | 21.7 |
| QUAKER 2006 | SSK | 5.60 | 2.68 | .30 | .160 | 21.0 |
| QUAKER 2006 | SSK | 4.04 | 1.68 | .42 | .224 | 29.4 |
| ARQUAD 2HT-75 | SSK | 4.70 | 3.18 | .34 | .181 | 23.8 |
| ARQUAD 2HT-75 | SSK | 3.95 | 2.02 | .32 | .171 | 22.4 |
| ARQUAD 2HT-75 | SSK | 3.56 | 2.00 | .29 | .155 | 20.3 |
| BEROCELL 579 | SSK | 4.88 | 2.75 | .39 | .208 | 27.3 |
| BEROCELL 579 | SSK | 4.52 | 2.69 | .39 | .208 | 27.3 |
| BEROCELL 579 | SSK | 3.81 | 2.00 | .30 | .160 | 21.0 |
| BEROCELL 582 | SSK | 5.21 | 2.59 | .45 | .240 | 31.5 |
| BEROCELL 582 | SSK | 3.76 | 1.83 | .41 | .219 | 28.7 |
| BEROCELL 582 | SSK | 3.51 | 1.76 | .35 | .187 | 24.5 |
| BEROCELL 584 | SSK | 4.10 | 1.86 | .45 | .240 | 31.5 |
| BEROCELL 584 | SSK | 3.22 | 1.45 | .42 | .224 | 29.4 |
| BEROCELL 584 | SSK | 2.90 | 1.40 | .38 | .203 | 26.6 |
| NONE | NSK | 11.50 | 8.62 | .43 | .229 | 30.1 |
| ETHOQUAD C/25 | NSK |  | 8.30 | .49 | .261 | 34.3 |
| ETHOQUAD C/25 | NSK |  | 7.65 | .44 | .235 | 30.8 |
| ETHOQUAD C/25 | NSK |  | 6.48 | .42 | .224 | 29.4 |
| ETHOQUAD 0/12 | NSK |  | 7.90 | .53 | .283 | 37.1 |
| ETHOQUAD 0/12 | NSK |  | 6.57 | .46 | .245 | 32.2 |
| ETHOQUAD 0/12 | NSK |  | 5.21 | .42 | .224 | 29.4 |
| ARQUAD 2HT-75 | NSK |  | 4.60 | .23 | .123 | 16.1 |
| ARQUAD 2HT-75 | NSK |  | 3.40 | .21 | .112 | 14.7 |
| ARQUAD 2HT-75 | NSK |  | 3.75 | .20 | .107 | 14.0 |

(SSK = Southern Softwood Kraft)
(NSK = Northern Softwood Kraft)

As can be seen from the above data adequate physical strength reduction is obtained by the debonders of this invention. Furthermore, at similar debonding efficiencies substantially improved water absorbency is generated by the compounds of this invention when compared, for example, to BEROCELL compounds which claim increased hydrophilicity for the debonding agents described in U.S. Pat. No. 4,144,122. These numbers hold true to varying levels of debonders. Even more importantly in some instances at lower levels of addition of the debonder of this invention, the hydrophilicity of the debonded pulp is actually greater than that of the untreated pulp.

The table also illustrates that the data, while changing slightly as the source of pulp changes, does apply in the same general order of magnitude.

EXAMPLE 2

When the compounds of this invention were tested for urine absorbency according to the procedure of Example 1, based upon a synthetic urine containing the following components:

| Compound | Concentration g/l |
|---|---|
| $KH_2PO_4$ F. W. = 136 | 0.681 |
| $CaH_4(PO_4)_2 \cdot H_2O$ F. W. = 252.1 | 0.309 |
| $MgSO_4 \cdot 7H_2O$ F. W. = 246.5 | 0.477 |
| $K_2SO_4$ F. W. = 174 | 1.333 |
| $Na_3PO_4 \cdot 12H_2O$ F. W. = 380 | 1.244 |
| NaCl F. W. = 58.4 | 4.441 |
| KCl F. W. = 74.5 | 3.161 |
| $NaN_3$ F. W. = 65 | 0.400 |
| Urea F. W. = 60 | 8.560 |
| A Non-Ionic Surfactant F. W. = 5000 | 0.100 |

The values obtained were again substantially greater than those of comparable commercially available debonders as can be seen from the table below:

| Additive | Pulp | % Addition | Synthetic Urine Absorbency (cm/sec ½) | (ml/sec ½) | Diaper Fluff Synthetic Urine Absorbency (ml/sec ½) |
|---|---|---|---|---|---|
| None | SSK |  | .64 | .341 | 44.8 |
| EMCOL CC-42 | SSK | 0.4 | .69 | .368 | 48.3 |
| EMCOL CC-42 | SSK | 1.0 | .66 | .352 | 46.2 |
| EMCOL CC-42 | SSK | 2.4 | .64 | .341 | 44.8 |
| ETHQUAD C/25 | SSK | 0.25 | .55 | .293 | 38.5 |
| ETHOQUAD C/25 | SSK | 0.5 | .55 | .293 | 38.5 |
| ETHOQUAD C/25 | SSK | 0.7 | .54 | .288 | 37.8 |
| ETHOQUAD C/25 | SSK | 1.0 | .53 | .283 | 37.1 |
| ETHOQUAD 0/12 | SSK | 0.4 | .65 | .347 | 45.5 |
| ETHOQUAD 0/12 | SSK | 1.0 | .56 | .299 | 39.2 |
| ETHOQUAD 0/12 | SSK | 2.4 | .61 | .325 | 42.7 |
| QUAKER 2006 | SSK | 0.4 | .33 | .176 | 23.1 |
| QUAKER 2006 | SSK | 1.0 | .35 | .187 | 24.5 |
| QUAKER 2006 | SSK | 2.4 | .40 | .213 | 28.0 |
| ARQUAD 2HT-75 | SSK | 0.4 | .25 | .133 | 17.5 |
| ARQUAD 2HT-75 | SSK | 1.0 | .20 | .107 | 14.0 |
| ARQUAD 2HT-75 | SSK | 2.4 | .22 | .117 | 15.4 |
| NONE | NSK |  | .45 | .240 | 31.5 |
| ETHOQUAD C/25 | NSK | 0.4 | .40 | .213 | 28.0 |
| ETHOQUAD C/25 | NSK | 1.0 | .39 | .208 | 27.3 |
| ETHOQUAD C/25 | NSK | 2.5 | .40 | .213 | 28.0 |
| ETHOQUAD C/25 | NSK | 0.4 | .43 | .229 | 30.1 |
| ETHOQUAD 0/12 | NSK | 1.0 | .39 | .208 | 27.3 |
| ETHOQUAD 0/12 | NSK | 2.5 | .34 | .181 | 23.8 |
| ARQUAD 2HT-75 | NSK | 0.4 | .18 | .096 | 12.6 |
| ARQUAD 2HT-75 | NSK | 1.0 | .14 | .075 | 9.8 |
| ARQUAD 2HT-75 | NSK | 2.5 | .15 | .080 | 10.5 |

As can be seen from the table above, substantial benefits are derived from the utilization of the debonders of this invention when the end product is designed to be fluff which is subsequently utilized in diapers or diaper related products.

Of course, as mentioned previously, the increase in hydrophilicity can have substantial additional benefits with regard to fluff in its conventional uses such as, for example, in sanitary napkins or other hygienic products.

EXAMPLE 3

In testing fluff pulps prepared according to the process of the present invention, the applicant has made use of several other definitive testing procedures. These are designated Absorbency Rate by Tube Test, The Instron Vertical Wicking Absorbency Rate, The Instron Vertical Wicking Absorbent Capacity, and the Saturated Capacity.

In the Absorbent Rate by Tube Test, 400#/3000 ft² basis weight pulp is fiberized in a Waring blender. This blender has specifically modified, dulled blades. There are 4 blades total, 2 bent up and 2 bent down. In addition a brass plate is attached to a rod protruding down from the lid to within ⅛ inch of the blades. Fiberization occurs for approximately 20 seconds which results in the pulp being 95% fiberized. 6.0 grams of the resulting fluff is packed into a 1.33 inch diameter tube to a height of 7.0 cm. At one end of the tube a heavy mesh screen is glued into place. The resulting density is uniform and approximately 0.096 gm/cc. The previously described synthetic urine is brought into contact with the screen bottom of the tube and the time recorded for the fluid to rise to the top of the fluff batt.

The Instron Vertical Wicking Capacity test measures the amount of fluid that a pulp fluff can wick in a given period of time. The Instron Vertical Wicking Rate test measures the rate of fluid absorption. A fluff batt of density 0.1 g/cc and basis weight 0.05 g/cm² is prepared from 400 lb/3000 ft² roll pulp utilizing a laboratory hammermill. The batt is mounted on the load cell on an Instron Tensile tester and lowered until it touches the liquid surface of a basin filled with the test solution. The chart recorder is run in a continuous mode giving a record of weight of fluid absorbed as a function of time. The rate is determined from the slope of this data over the first 30 seconds of the test. The capacity is the volume absorbed at 15 minutes.

The Saturated Capacity test measures the capacity of the fluff batt to retain fluid under pressure. The preweighed fluff batt sample is initially immersed in the test solution until saturated. It is then carefully set on a screen and vacuum of 0.5 PSI applied for 5 minutes after which it is weighed again. The difference in weights divided by the dry weight is defined as the saturated capacity.

All fluff samples were prepared from pulp made from the same lot of Southern Softwood Kraft, treated with the test additives in the same manner to the same burst (70 PSI) and fiberized on the same hammermill. The superior absorbent capacity of the samples treated with ETHOQUAD C/25 ETHOQUAD 0/12 and EMCOL CC-42 relative to the BEROCELL 584 samples is readily apparent from the Table below. Also, the Table demonstrates that ETHOQUAD C/25 and EMCOL CC-42 evidence a better absorbent rate than the comparison prior art component.

| Sample | Tube Test (minutes) | Instron Vertical Wicking Rate (ml/g) | Instron Vertical Wicking Capacity (ml/g) | Saturated Capacity (g/g) |
|---|---|---|---|---|
| Control (no additive) | 0.5 | 52 | 498 | 6.6 |
| ETHOQUAD 0/12 | 0.9 | 38 | 396 | 6.8 |
| ETHOQUAD C/25 | 0.5 | 49 | 466 | 6.3 |
| EMCOL CC-42 | 0.6 | 49 | 483 | 6.6 |

| Sample | Tube Test (minutes) | Instron Vertical Wicking Rate (ml/g) | Instron Vertical Wicking Capacity (ml/g) | Saturated Capacity (g/g) |
|---|---|---|---|---|
| BEROCELL 584 | 0.7 | 39 | 349 | 6.5 |

EXAMPLE 4

The superiority of the structural class of hydrophilic debonders described in this invention over the debonders described in U.S. Pat. No. 4,144,122 was shown by the following direct comparison. Modifications of the procedure described in U.S. Pat. No. 3,972,855 were utilized to form the following products:

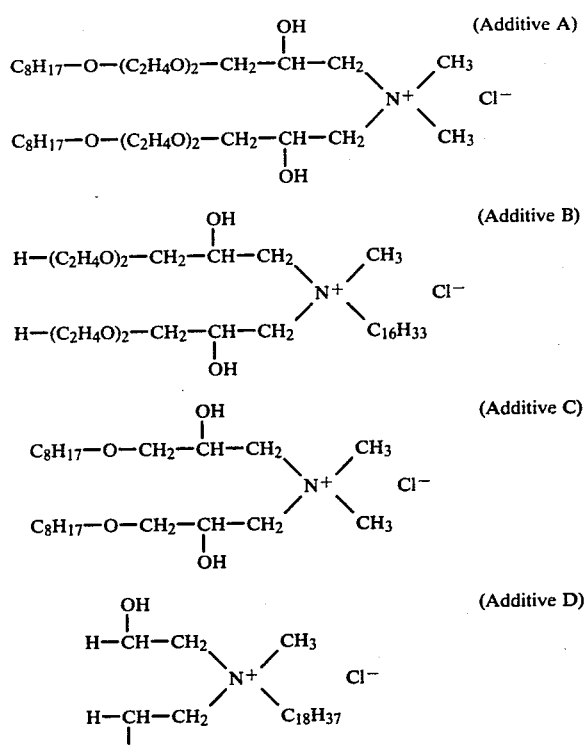

Additive D was obtained from Armak Chemical Co. Chicago, IL and is sold under the name ETHOQUAD 18/12

Here Additive A and Additive C are from the same family of hydrophilic debonders. Additive A also fits the description of the hydrophilic debonders given in U.S. Pat. No. 4,144,122, and additive C is described in U.S. Pat. No. 3,972,855. Additive B and Additive D are included in the family of chemicals described by this invention. While not identical, Additive A and Additive B are closely related in their chemical composition; i.e., the presence of two ether groups in Additive A which is expected to improve its hydrophilicity and the separation in additive B of the ethylene oxide units from the alkyl group. The same is true of Additive C and Additive D. Thus, comparing the hydrophilic debonding characteristics of Additive A with Additive B and Additive C with Additive D allows for the direct comparison of the structural differences of the debonders used in this invention compared to the closest prior art.

Pulp samples were prepared as described in Example 3. The absorbency rate by Tube Test and Strip Test were performed as previously described. The data in the table clearly demonstrates the hydrophilic debonding superiority of the structure of this invention.

| | Additive A | Additive B | Additive C | Additive D |
|---|---|---|---|---|
| Burst (psi) | 67 | 66 | 68 | 67 |
| Absorbency by Strip Test (cm/sec ½) | 101 | 122 | 87 | 96 |
| Absorbency by Tube Test (minutes) | 0.8 | 0.5 | 1.4 | 1.2 |

What is claimed is:

1. A wood pulp consisting essentially of a hydrophilic debonder having the general formula:

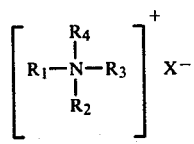

wherein:
$R_1$ = methyl, ethyl, propyl, hydrogen or hydroxyethyl,
$R_2$ = methyl, ethyl, propyl or (ethylene oxide)$_n$ where n = 1 to 50,
$R_3$ = aliphatic chain of at least 4 carbon items,
$R_4$ = (ethylene oxide)$_n$ or (propylene oxide)$_n$ with n = 1 to 50,
X = Cl, I, Br, SO$_4$, PO$_4$, CH$_3$CO$_2$
said debonder present at the level of 0.1% to 5.0% by weight of the dry cellulosic material in an amount sufficient to increase the water and/or urine absorbency.

2. A process for treating cellulose pulp fibers to reduce interfiber bonding while preserving the hydrophilicity of the pulp comprising adding to a cellulose pulp fiber slurry prior to or during the formation of the slurry into a web a debonder consisting essentially of quaternary ammonium compound having the formula:

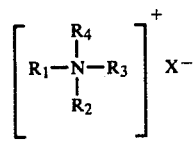

wherein:
$R_1$ = methyl, ethyl, propylene, hydrogen or hydroxyethyl,
$R_2$ = methyl, ethyl, propyl or (ethylene oxide)$_n$ where n = 1 to 50,
$R_3$ = aliphatic chain of at least 4 carbon atoms,
$R_4$ = (ethylene oxide)$_n$ or (propylene oxide)$_n$ with n = 1 to 50,
X = Cl, I, Br, SO$_4$, PO$_4$, CH$_3$CO$_2$
and forming and drying said web, said quaternary ammonium compound added at a level of 0.1% to 5.0% by weight of the dry cellulosic material in an amount sufficient to increase the water and/or urine absorbency.

3. The process according to claim 2 wherein the quaternary ammonium compound applied to the fibers is from about 0.05% to 5.0% based on the dry weight of the cellulose.

4. The process according to claim 2 in which the quaternary ammonium compound is added by spraying a solution thereof on the web and drying the web.

5. The process according to claim 2 wherein the quaternary ammonium compound is added to the slurry of cellulosic pulp fibers and the pulp is subsequently dried.

6. A process according to claim 2 in which the web is fiberized into cellulose fluff.

7. A process according to claim 2 in which the quaternary ammonium compound is added during formation of the cellulose pulp fiber slurry into a web.

8. An absorbent fluff containing the hydrophilic debonder of claim 1.

9. A diaper containing an absorbent fluff with a hydrophilic debonder said debonder consisting essentially of a compound having the general formula:

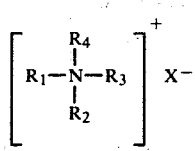

wherein:
R$_1$=methyl, ethyl, propyl, hydrogen or hydroxyethyl,
R$_2$=methyl, ethyl, propyl or (ethylene oxide)$_n$ where n=1 to 50,
R$_3$=aliphatic chain of at least 4 carbon atoms,
R$_4$=(ethylene oxide)$_n$ or (propylene oxide)$_n$ with n=1 to 50,
X=Cl, I, Br, SO$_4$, PO$_4$, CH$_3$CO$_2$ said debonder being present at the level of 0.1% to 5.0% by weight of the dry cellulosic material in an amount sufficient to increase the water and/or urine absorbency.

10. An absorbent cellulosic based sheet stock with a hydrophilic debonder said debonder consisting essentially of the general formula:

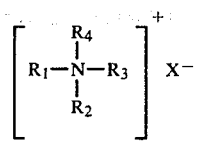

wherein:
R$_1$=methyl, ethyl, propyl, hydrogen or hydroxyethyl,
R$_2$=methyl, ethyl, propyl or (ethylene oxide)$_n$ where n=1 to 50,
R$_3$=aliphatic chain of at least 4 carbon atoms,
R$_4$=(ethylene oxide)$_n$ or (propylene oxide)$_n$ with n=1 to 50,
X=Cl, I, Br, SO$_4$, PO$_4$, CH$_3$CO$_2$ said debonder being present at the level of 0.1% to 5.0% by weight of the dry cellulosic material in an amount sufficient to increase the water and/or urine absorbency.

* * * * *